(12) United States Patent
Samanwong et al.

(10) Patent No.: US 9,717,244 B2
(45) Date of Patent: Aug. 1, 2017

(54) METHODS OF WEED CONTROL IN PINEAPPLE

(71) Applicant: Dow AgroSciences LLC, Indianapolis, IN (US)

(72) Inventors: Somsak Samanwong, Nonthaburi (TH); Richard K. Mann, Franklin, IN (US); Lap Nguyen, Ho Chi Minh (VN)

(73) Assignee: Dow AgroSciences LLC, Indianapolis, IN (US)

( * ) Notice: Subject to any disclaimer, the term of this patent is extended or adjusted under 35 U.S.C. 154(b) by 32 days.

(21) Appl. No.: 14/185,260

(22) Filed: Feb. 20, 2014

(65) Prior Publication Data

US 2014/0243198 A1 Aug. 28, 2014

Related U.S. Application Data

(60) Provisional application No. 61/768,790, filed on Feb. 25, 2013.

(51) Int. Cl.
*A01N 43/90* (2006.01)

(52) U.S. Cl.
CPC .................................. *A01N 43/90* (2013.01)

(58) Field of Classification Search
CPC ........ A01N 43/40; A01N 43/90; A01N 43/54; A01N 43/50; A01N 43/82; A01N 41/06; A01N 43/36; A01N 43/58; A01N 43/707
See application file for complete search history.

(56) References Cited

U.S. PATENT DOCUMENTS

| | | | |
|---|---|---|---|
| 5,858,924 | A | 1/1999 | Ehr et al. |
| 7,314,849 | B2 | 1/2008 | Balko et al. |
| 7,432,227 | B2 | 10/2008 | Balko et al. |
| 7,863,220 | B2 | 1/2011 | Clark et al. |
| 8,071,508 | B2 | 12/2011 | Keenan et al. |
| 8,203,033 | B2 | 6/2012 | McCutchen et al. |
| 2002/0055435 | A1 | 5/2002 | Baltruschat et al. |
| 2004/0102321 | A1 | 5/2004 | Feucht et al. |
| 2006/0167018 | A1 | 7/2006 | Zagar et al. |
| 2006/0183637 | A1 | 8/2006 | Loughner et al. |
| 2008/0153704 | A1 | 6/2008 | Yamaji et al. |
| 2010/0016158 | A1 | 1/2010 | Kilian et al. |
| 2010/0048399 | A1 | 2/2010 | Hacker et al. |
| 2010/0099564 | A1 | 4/2010 | Hacker et al. |
| 2010/0190794 | A1 | 7/2010 | Hupe et al. |
| 2010/0279862 | A1 | 11/2010 | Bickers et al. |
| 2010/0279864 | A1 | 11/2010 | Mann et al. |
| 2010/0285959 | A1 | 11/2010 | Armel et al. |
| 2010/0304973 | A1 | 12/2010 | Rosinger et al. |
| 2010/0311588 | A1 | 12/2010 | Gatzweiler et al. |
| 2011/0092367 | A1 | 4/2011 | Griveau et al. |
| 2011/0098182 | A1 | 4/2011 | Mann et al. |
| 2011/0183845 | A1 | 7/2011 | Loughner et al. |
| 2011/0190134 | A1 | 8/2011 | Jousseaume et al. |
| 2011/0190135 | A1 | 8/2011 | Mann et al. |
| 2011/0190136 | A1 | 8/2011 | Hufnagl et al. |
| 2011/0287935 | A1 | 11/2011 | Patzoldt et al. |
| 2011/0294663 | A1 | 12/2011 | Hacker et al. |
| 2012/0071320 | A1 | 3/2012 | Atkinson et al. |
| 2012/0238449 | A1 | 9/2012 | Mann |
| 2012/0284812 | A1 | 11/2012 | Mankin et al. |
| 2014/0031214 | A1 | 1/2014 | Yerkes et al. |

FOREIGN PATENT DOCUMENTS

| | | |
|---|---|---|
| CN | 101647450 | 2/2010 |
| CN | 101861867 A | 10/2010 |
| CN | 102132702 | 1/2013 |
| EP | 1313369 | 6/2005 |
| WO | 2009103451 | 8/2009 |
| WO | 2010009819 | 1/2010 |
| WO | 2010017921 | 2/2010 |
| WO | 2010046422 | 4/2010 |
| WO | 2010136165 | 12/2010 |
| WO | 2011097187 | 8/2011 |
| WO | 2011113052 | 9/2011 |
| WO | 2012037425 | 3/2012 |
| WO | 2012150333 | 11/2012 |

OTHER PUBLICATIONS

Verdict 520 haloxyfop 2007 label. [downloaded on Jul. 23, 2015 from the website http://msdssearch.dow.com/PublishedLiteratureDAS/dh_091b/0901b8038091ba07.pdf?filepath=au/pdfs/noreg/012-10039.pdf&fromPage=GetDoc].*
International Search Report and Written Opinion, dated May 22, 2014, in corresponding International Application No. PCT/US14/17370, 8 pages.
Farm Chemical International, Crop Protection Database, "Penoxsulam," available at http://www.farmchemicalsinternational.com/crop-protection-database/#/product/detail/424174/ (accessed on May 27, 2014).
Tomlin, C. D. S., Ed., The Pesticide Manual: A World Compendium, "Penoxsulam," 15th ed., BCPC: Alton, 2009, pp. 874-875.

\* cited by examiner

*Primary Examiner* — Sue Liu
*Assistant Examiner* — Thor Nielsen
(74) *Attorney, Agent, or Firm* — Michael R. Asam; Meunier Carlin & Curfman LLC

(57) ABSTRACT

Disclosed herein are methods of controlling undesirable vegetation in pineapple, which comprise applying to vegetation or an area adjacent the vegetation or applying to soil to prevent the emergence or growth of vegetation (a) penoxsulam or an agriculturally acceptable salt thereof. The methods can further comprise applying (b) a second pesticide or an agriculturally acceptable salt or ester thereof to the vegetation or the area adjacent the vegetation or to the soil adjacent thereto. In some embodiments, (b) includes an ACCase inhibitor such as cyhalofop-butyl, haloxyfop-P-methyl, fluazifop-P-butyl, or combinations thereof.

20 Claims, No Drawings

METHODS OF WEED CONTROL IN PINEAPPLE

CROSS REFERENCE TO RELATED APPLICATIONS

This application claims the benefit of U.S. Provisional Patent Application Ser. No. 61/768,790 filed Feb. 25, 2013, the disclosure of which is expressly incorporated herein by reference.

FIELD OF THE DISCLOSURE

The present disclosure also relates to methods for controlling undesirable vegetation in pineapple.

BACKGROUND

Many recurring problems in agriculture involve controlling growth of undesirable vegetation that can, for instance, inhibit crop growth. To help control undesirable vegetation, researchers have produced a variety of chemicals and chemical formulations effective in controlling such unwanted growth. However, a continuing need exists for new compositions and methods to control growth of undesirable vegetation.

In particular, pineapple is a significant cash crop in many regions of the world, including Southeast Asia, the Americas, and Africa. Currently, pineapple productivity is significantly limited by the growth of undesirable vegetation. Existing methods of controlling undesirable vegetation in pineapple suffer from significant shortcomings For example, in Thailand, bromacil and diuron are applied in combination, both pre-emergence and post-emergence, to control weeds in pineapple. However, post-emergence application of bromacil and diuron results in significant phytotoxic effects in pineapple.

SUMMARY OF THE DISCLOSURE

The present disclosure is based on the unexpected discovery that (a) penoxsulam or an agriculturally acceptable salt thereof can be applied to pineapple to control undesirable vegetation without significant crop damage. Accordingly, the present disclosure relates to methods of controlling undesirable vegetation in pineapple, which comprise applying to vegetation or an area adjacent the vegetation or applying to soil to prevent the emergence or growth of vegetation (a) penoxsulam or an agriculturally acceptable salt thereof. In some embodiments, (a) is applied in an amount of from 5-50 grams active ingredient per hectare (g ai/ha) (e.g., from 10-30 g ai/ha).

The method can further comprise applying (b) a second pesticide or an agriculturally acceptable salt or ester thereof to the vegetation or the area adjacent the vegetation, or to the soil adjacent thereto, either in combination with, or sequentially to, penoxsulam. In some embodiments, (b) includes an ACCase (acetyl Coenzyme A carboxylase) inhibitor. Exemplary ACCase inhibitors include, but are not limited to, cyhalofop, haloxyfop, fluazifop, clodinafop, diclofop, propaquizafop, quizalofop, alloxydim, butoxydim, clethodim, profoxydim, sethoxydim, tepraloxydim, tralkoxydim, pinoxaden, agriculturally acceptable salts and esters thereof, and combinations thereof. For example, in some cases, (b) can comprise cyhalofop (e.g., cyhalofop-butyl), haloxyfop (e.g., haloxyfop-P-methyl), fluazifop (e.g., fluazifop-P-butyl), or combinations thereof.

Pesticides (a) and (b) can applied in a weight ratio of (a) to (b) from 1:100 to 2:1 (e.g., from 1:12 to 1:2, from 1:10 to 1:2, from 1:12 to 1:4, from 1:10 to 1:4, or from 1:8 to 1:4). In some embodiments, (a) is applied in an amount of from 5 to 50 g ai/ha ((e.g., (a) can be applied in an amount of from 12.5 to 25 g ai/ha). In some embodiments, (b) is applied in an amount of from 25 to 500 g ai/ha (e.g., from 40 to 200 g ai/ha, from 75 to 150 g ai/ha, or from 84 to 150 g ai/ha).

The undesirable vegetation can be a broadleaf weed, grass weed, sedge weed, or combinations thereof. In certain embodiments, the undesirable vegetation includes praxelis, oriental fountain grass, mission grass, broadleaf buttonweed, morning-glory, crabgrass, Guinea grass, crowfoot grass, slender amaranth, Southern sandbur, signalgrass, sweet broomweed and combinations thereof. In some embodiments, (a) and (b), when present, are applied post-emergence to the undesirable vegetation.

The description below sets forth details of one or more embodiments of the present disclosure. Other features, objects, and advantages will be apparent from the description and from the claims.

DETAILED DESCRIPTION

The present disclosure relates to methods of controlling undesirable vegetation in pineapple, which comprise applying to vegetation or an area adjacent the vegetation or applying to soil to prevent the emergence or growth of vegetation (a) penoxsulam or an agriculturally acceptable salt thereof.

The term "herbicide," as used herein, means an active ingredient that kills, controls, or otherwise adversely modifies the growth of vegetation. A "herbicidally effective amount" is an amount of an active ingredient that causes a "herbicidal effect," i.e., an adversely modifying effect and includes deviations from, for instance, natural development, killing, regulation, desiccation, and retardation. The terms "plants" and "vegetation" can include, for instance, germinant seeds, emerging seedlings, and established vegetation.

Penoxsulam

Methods of the present disclosure can involve applying penoxsulam (i.e., 2-(2,2-difluoroethoxy)-N-(5,8-dimethoxy[1,2,4]triazolo[1,5-c]pyrimidin-2-yl)-6-trifluoromethyl)benzenesulfonamide) or an agriculturally acceptable salt thereof. Penoxsulam, shown below, is a triazolopyrimidine sulfonamide herbicide that provides broad-spectrum control of many annual, biannual, and perennial weeds. Penoxsulam, as well as methods of preparing penoxsulam, are known in the art. See, for example, U.S. Pat. No. 5,858,924 to Loughner et al.

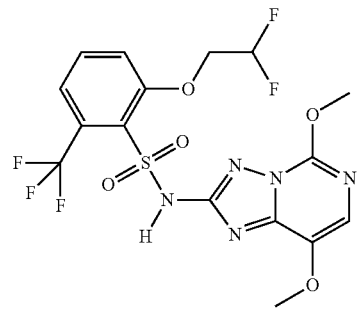 [SMILES: COc1cnc(OC)n2nc(NS(=O)(=O)c3c(OCC(F)F)cccc3C(F)(F)F)nc12]

In some embodiments, penoxsulam can be provided as an agriculturally acceptable salt of penoxsulam. Exemplary agriculturally acceptable salts of penoxsulam include, but are not limited to, sodium salts, potassium salts, ammonium salts or substituted ammonium salts, in particular mono-, di- and tri-$C_1$-$C_8$-alkylammonium salts such as methyl ammonium, dimethylammonium and isopropylammonium, mono-, di- and tri-hydroxy-$C_2$-$C_8$-alkylammonium salts such as hydroxyethylammonium, di(hydroxyethyl)ammonium, tri(hydroxyethyl)ammonium, hydroxypropylammonium, di(hydroxypropyl)ammonium and tri(hydroxypropyl)ammonium salts, olamine salts, and diglycolamine salts.

Penoxsulam can be used to control broadleaf weeds in, for instance, rice, sorghum, corn, tree and vine crops, lawns (e.g., residential, industrial, and institutional), golf courses, parks, cemeteries, athletic fields, sod farms, range and pasture, rights-of-way, roadsides, and other crop and non-crop uses. Its herbicidal activity is described in Tomlin, C. D. S., Ed. *The Pesticide Manual: A World Compendium*, 15th ed.; BCPC: Alton, 2009 (hereafter "The Pesticide Manual, Fifteenth Edition, 2009"). Penoxsulam is or has been commercially available, for example, from Dow AgroSciences LLC under the trademarks RAINBOW®, CLIPPER®, FENCER®, SAPPHIRE®, GRASP®, VIPER®, BENGALA®, and GRANITE®, and from SePRO Corporation under the trademark GALLEON®.

Penoxsulam or an agriculturally acceptable salt thereof can be applied to vegetation or an area adjacent the vegetation or applied to soil to prevent the emergence or growth of vegetation in an amount sufficient to induce a herbicidal effect. In certain embodiments, penoxsulam is applied in an amount sufficient to control undesirable vegetation in pineapple without causing significant crop damage. In some embodiments, the penoxsulam or agriculturally acceptable salt thereof is applied to vegetation or an area adjacent the vegetation or applied to soil to prevent the emergence or growth of vegetation in an amount of 5 grams of active ingredient per hectare (g ai/ha) or greater (e.g., 6 g ai/ha or greater, 7 g ai/ha or greater, 7.5 g ai/ha or greater, 8 g ai/ha or greater, 9 g ai/ha or greater, 10 g ai/ha or greater, 11 g ai/ha or greater, 12 g ai/ha or greater, 13 g ai/ha or greater, 14 g ai/ha or greater, 15 g ai/ha or greater, 16 g ai/ha or greater, 17 g ai/ha or greater, 18 g ai/ha or greater, 19 g ai/ha or greater, 20 g ai/ha or greater, 21 g ai/ha or greater, 22 g ai/ha or greater, 23 g ai/ha or greater, 24 g ai/ha or greater, 25 g ai/ha or greater, 26 g ai/ha or greater, 27 g ai/ha or greater, 28 g ai/ha or greater, 29 g ai/ha or greater, 30 g ai/ha or greater, 31 g ai/ha or greater, 32 g ai/ha or greater, 33 g ai/ha or greater, 34 g ai/ha or greater, 35 g ai/ha or greater, 36 g ai/ha or greater, 37 g ai/ha or greater, 38 g ai/ha or greater, 39 g ai/ha or greater, 40 g ai/ha or greater, 41 g ai/ha or greater, 42 g ai/ha or greater, 43 g ai/ha or greater, 44 g ai/ha or greater, 45 g ai/ha or greater, 46 g ai/ha or greater, 47 g ai/ha or greater, 48 g ai/ha or greater, or 49 g ai/ha or greater). In some embodiments, the penoxsulam or agriculturally acceptable salt thereof is applied to vegetation or an area adjacent the vegetation or applied to soil to prevent the emergence or growth of vegetation in an amount of 50 g ai/ha or less (e.g., 49 g ai/ha or less, 48 g ai/ha or less, 47 g ai/ha or less, 46 g ai/ha or less, 45 g ai/ha or less, 44 g ai/ha or less, 43 g ai/ha or less, 42 g ai/ha or less, 41 g ai/ha or less, 40 g ai/ha or less, 39 g ai/ha or less, 38 g ai/ha or less, 37 g ai/ha or less, 36 g ai/ha or less, 35 g ai/ha or less, 34 g ai/ha or less, 33 g ai/ha or less, 32 g ai/ha or less, 31 g ai/ha or less, 30 g ai/ha or less, 29 g ai/ha or less, 28 g ai/ha or less, 27 g ai/ha or less, 26 g ai/ha or less, 25 g ai/ha or less, 24 g ai/ha or less, 23 g ai/ha or less, 22 g ai/ha or less, 21 g ai/ha or less, 20 g ai/ha or less, 19 g ai/ha or less, 18 g ai/ha or less, 17 g ai/ha or less, 16 g ai/ha or less, 15 g ai/ha or less, 14 g ai/ha or less, 13 g ai/ha or less, 12 g ai/ha or less, 11 g ai/ha or less, 10 g ai/ha or less, 9 g ai/ha or less, 8 g ai/ha or less, 7.5 g ai/ha or less, 7 g ai/ha or less, or 6 g ai/ha or less).

Penoxsulam can be applied to vegetation or an area adjacent the vegetation or applied to soil to prevent the emergence or growth of vegetation in an amount ranging from any of the minimum values described above to any of the maximum values described above.

In some embodiments, the penoxsulam or agriculturally acceptable salt thereof is applied to vegetation or an area adjacent the vegetation or applied to soil to prevent the emergence or growth of vegetation in an amount of from 5 to 50 g ai/ha (e.g., from 6 to 45 g ai/ha, from 7 to 40 g ai/ha, from 8 to 35 g ai/ha, or from 10 to 30 g ai/ha).

The method described herein can further comprise applying (b) a second pesticide, or an agriculturally acceptable salt or ester thereof, to the vegetation or the area adjacent the vegetation, or to the soil adjacent thereto. In some embodiments, (b) includes an ACCase inhibitor. Exemplary ACCase inhibitors include, but are not limited to, cyhalofop, haloxyfop, fluazifop, clodinafop, diclofop, propaquizafop, quizalofop, alloxydim, butoxydim, clethodim, profoxydim, sethoxydim, tepraloxydim, tralkoxydim, pinoxaden, agriculturally acceptable salts and esters thereof, and combinations thereof. In certain embodiments, (b) can comprise cyhalofop, haloxyfop, fluazifop, agriculturally acceptable salts or esters thereof, or combinations thereof.

Cyhalofop

Methods of the present disclosure can involve applying cyhalofop or an agriculturally acceptable salt or ester thereof Cyhalofop (i.e., 2-[4-(4-cyano-2-fluoro-4-phenoxy)phenoxy]propionic acid) is a herbicide that inhibits the biosynthesis of lipids through inhibition of acetyl CoA carboxylase (ACCase). Cyhalofop can be used to control annual grasses, for instance, in rice. Its herbicidal activity is described in *The Pesticide Manual*, Fifteenth Edition, 2009.

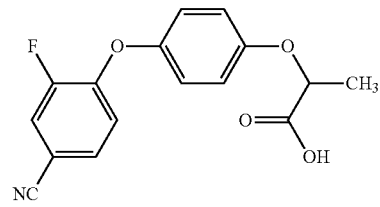 [SMILES: CC(Oc1ccc(Oc2ccc(C#N)cc2F)cc1)C(=O)O]

Cyhalofop can be provided in its acid form (as shown above) or as an agriculturally acceptable salt or ester thereof. Exemplary agriculturally acceptable salts of cyhalofop include, but are not limited to, sodium salts, potassium salts, ammonium salts or substituted ammonium salts, in particular mono-, di- and tri-$C_1$-$C_8$-alkylammonium salts such as methyl ammonium, dimethylammonium and isopropylammonium, mono-, di- and tri-hydroxy-$C_2$-$C_8$-alkylammonium salts such as hydroxyethylammonium, di(hydroxyethyl)ammonium, tri(hydroxyethyl)ammonium, hydroxypropylammonium, di(hydroxypropyl)ammonium and tri(hydroxypropyl)ammonium salts, olamine salts, and diglycolamine salts. In certain embodiments, cyhalofop is provided as an agriculturally acceptable ester. Suitable esters include, but are not limited to, $C_1$-$C_8$-alkyl esters and $C_1$-$C_4$-alkoxy-$C_2$-$C_4$-alkyl esters, such as methyl esters, ethyl esters, isopropyl, butyl, hexyl, heptyl, isoheptyl, isooctyl, 2-ethylhexyl and butoxyethyl esters, and aryl esters such as benzyl. An exemplary agriculturally acceptable ester of cyhalofop can include cyhalofopbutyl.

Cyhalofop or agriculturally acceptable salts or esters thereof are or have been commercially available, for example, under the trademarks CLINCHER® (by Dow AgroSciences LLC), BEAUTY® (by Fertiagro Pte. Ltd.), CLARON® (by IPESA S.A.), BENDAS® (by Wangs Crop-Science Co., Ltd.), MYCORIX® (by AgriSciences Co., Ltd.), TRINCHERA® (by Invesa S.A.), and WICLIN® (by Willowood Ltd.).

Haloxyfop

Methods of the present disclosure can involve applying haloxyfop or an agriculturally acceptable salt or ester thereof Haloxyfop (i.e., 2-[4-[(3-chloro-5-(trifluoromethyl)-2-pyridyloxy)phenoxy]propionic acid) is a herbicide that inhibits the biosynthesis of lipids through inhibition of acetyl CoA carboxylase (ACCase). Haloxyfop can be used, for example, to control annual grasses in broad leaf crops. Its herbicidal activity is described in *The Pesticide Manual, Fifteenth Edition*, 2009.

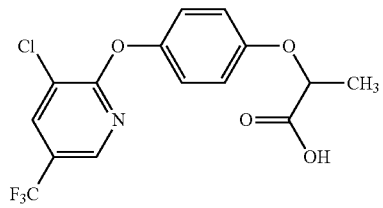 [SMILES: CC(Oc1ccc(Oc2ncc(C(F)(F)F)cc2Cl)cc1)C(=O)O]

Haloxyfop can be provided in its acid form (as shown above) or as an agriculturally acceptable salt or ester thereof. Exemplary agriculturally acceptable salts of haloxyfop include, but are not limited to, sodium salts, potassium salts, ammonium salts or substituted ammonium salts, in particular mono-, di- and tri-$C_1$-$C_8$-alkylammonium salts such as methyl ammonium, dimethylammonium and isopropylammonium, mono-, di- and tri-hydroxy-$C_2$-$C_8$-alkylammonium salts such as hydroxyethylammonium, di(hydroxyethyl)ammonium, tri(hydroxyethyl)ammonium, hydroxypropylammonium, di(hydroxypropyl)ammonium and tri(hydroxypropyl)ammonium salts, olamine salts, and diglycolamine salts. In certain embodiments, haloxyfop is provided as an agriculturally acceptable ester. Suitable esters include, but are not limited to, $C_1$-$C_8$-alkyl esters and $C_1$-$C_4$-alkoxy-$C_2$-$C_4$-alkyl esters, such as methyl esters, ethyl esters, isopropyl, butyl, hexyl, heptyl, isoheptyl, isooctyl, 2-ethylhexyl and butoxyethyl esters, and aryl esters such as benzyl. Exemplary agriculturally acceptable esters of haloxyfop include haloxyfop-methyl, haloxyfop-etotyl, and haloxyfop-R-methyl.

Haloxyfop or agriculturally acceptable salts or esters thereof are or have been commercially available, for example, under the trademarks HALCYON® (by Pacific Agriscience Pte. Ltd), GRANTE® (by Suzhou Eagro Ltd.), WOPRO-HALOXYFOP® (by B.V. Industrie- & Handelsonderneming Simonis), and IGNITE® (by Zelam Ltd.).

Fluazifop

Methods of the present disclosure can involve applying fluazifop or an agriculturally acceptable salt or ester thereof Fluazifop (i.e., 2-{4-[5-(trifluoromethyl)-2-pyridyloxy]phenoxy}propionic acid) is a herbicide that inhibits the biosynthesis of lipids through inhibition of acetyl CoA carboxylase (ACCase). Fluazifop can be used, for example, to control annual grasses in asparagus, carrots, cotton, dry bulb onions, soybeans, spinach, sweet potatoes, and ornamentals. Its herbicidal activity is described in *The Pesticide Manual*, Fifteenth Edition, 2009.

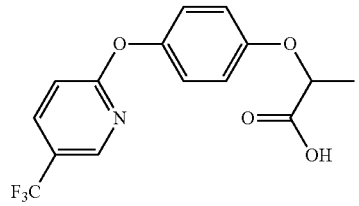 [SMILES: CC(Oc1ccc(Oc2ccc(C(F)(F)F)cn2)cc1)C(=O)O]

Fluazifop can be provided in its acid form (as shown above) or as an agriculturally acceptable salt or ester thereof. Exemplary agriculturally acceptable salts of fluazifop include, but are not limited to, sodium salts, potassium salts, ammonium salts or substituted ammonium salts, in particular mono-, di- and tri-$C_1$-$C_8$-alkylammonium salts such as methyl ammonium, dimethylammonium and isopropylammonium, mono-, di- and tri-hydroxy-$C_2$-$C_8$-alkylammonium salts such as hydroxyethylammonium, di(hydroxyethyl)ammonium, tri(hydroxyethyl)ammonium, hydroxypropylammonium, di(hydroxypropyl)ammonium and tri(hydroxypropyl)ammonium salts, olamine salts, and diglycolamine salts. In certain embodiments, fluazifop is provided as an agriculturally acceptable ester. Suitable esters include, but are not limited to, $C_1$-$C_8$-alkyl esters and $C_1$-$C_4$-alkoxy-$C_2$-$C_4$-alkyl esters, such as methyl esters, ethyl esters, isopropyl, butyl, hexyl, heptyl, isoheptyl, isooctyl, 2-ethylhexyl and butoxyethyl esters, and aryl esters such as benzyl. Exemplary agriculturally acceptable esters of fluazifop include fluazifop-P-butyl.

Fluazifop or agriculturally acceptable salts or esters thereof are or have been commercially available, for example, under the trademarks FUSILADE DX® (by Syngenta), FUSILADE FORTE® (by Syngenta), FUSILADE II® (by Syngenta), FUSILADE MAX® (by Syngenta), VENTURE® (by Syngenta), AGROFUSIL® (by Agro-Care Chemical Industry Group Limited), FLUAZUCARE® (by Agro-Care Chemical Industry Group Limited), ISOFOB® (by Cam For Agrochemicals), BOREALIA® (by Chema Industries), BRACE FORTE® (by Hektas Ticaret T.A.S.), BRACE SUPER° (by Hektas Ticaret T.A.S.), ORNAMEC 170® (by PBI/Gordon Corp.), ORNAMEC OVER-THE-TOP® (by PBI/Gordon Corp.), WILLIFOP® (by Willowood Ltd.), HACHE UNO SUPER® (by Ishihara Sangyo Kaisha, Ltd.), LEGAT® (by Parijat), LISTO® (by Ishihara Sangyo Kaisha, Ltd.), ONECIDE® (by Ishihara Sangyo Kaisha, Ltd.), and WOPRO-FLUAZIFOP® (by B.V. Industrie- & Handelsonderneming Simonis).

The second pesticide (b) or an agriculturally acceptable salt or ester thereof can be applied to vegetation or an area adjacent the vegetation or applied to soil to prevent the emergence or growth of vegetation in an amount sufficient to induce a herbicidal effect. In certain embodiments, (b) or an agriculturally acceptable salt or ester thereof is applied in an amount sufficient to control undesirable vegetation in pineapple without causing significant crop damage. In some embodiments, the (b) or agriculturally acceptable salt or ester thereof is applied to vegetation or an area adjacent the vegetation or applied to soil to prevent the emergence or growth of vegetation in an amount of 25 grams active ingredient per hectare (g ai/ha) or greater (e.g., 30 g ai/ha or greater, 35 g ai/ha or greater, 40 g ai/ha or greater, 45 g ai/ha or greater, 50 g ai/ha or greater, 55 g ai/ha or greater, 60 g ai/ha or greater, 65 g ai/ha or greater, 70 g ai/ha or greater, 75 g ai/ha or greater, 80 g ai/ha or greater, 85 g ai/ha or greater, 90 g ai/ha or greater, 95 g ai/ha or greater, 100 g ai/ha or greater, 105 g ai/ha or greater, 110 g ai/ha or greater, 115 g ai/ha or greater, 120 g ai/ha or greater, 125 g ai/ha or greater, 130 g ai/ha or greater, 135 g ai/ha or greater, 140 g ai/ha or greater, 145 g ai/ha or greater, 150 g ai/ha or greater, 155 g ai/ha or greater, 160 g ai/ha or greater, 165 g ai/ha or greater, 170 g ai/ha or greater, 175 g ai/ha or greater, 180 g ai/ha or greater, 185 g ai/ha or greater, 190 g ai/ha or greater, 195 g ai/ha or greater, 200 g ai/ha or greater, 210 g ai/ha or greater, 220 g ai/ha or greater, 230 g ai/ha or greater, 240 g ai/ha or greater, 250 g ai/ha or greater, 260 g ai/ha or greater, 270 g ai/ha or greater, 280 g ai/ha or greater, 290 g ai/ha or greater, 300 g ai/ha or greater, 310 g ai/ha or greater, 320 g ai/ha or greater, 330 g ai/ha or greater, 340 g ai/ha or greater, 350 g ai/ha or greater, 360 g ai/ha or greater, 370 g ai/ha or greater, 380 g ai/ha or greater, 390 g ai/ha or greater, 400 g ai/ha or greater, 410 g ai/ha or greater, 420 g ai/ha or greater, 430 g ai/ha or greater, 440 g ai/ha or greater, 450 g ai/ha or greater, 460 g ai/ha or greater, 470 g ai/ha or greater, 480 g ai/ha or greater, or 490 g ai/ha or greater). In some embodiments, the (b) or agriculturally acceptable salt or ester thereof is applied to vegetation or an area adjacent the vegetation or applied to soil to prevent the emergence or growth of vegetation in an amount of 500 g ai/ha or less (e.g., 490 g ai/ha or less, 480 g ai/ha or less, 470 g ai/ha or less, 460 g ai/ha or less, 450 g ai/ha or less, 440 g ai/ha or less, 430 g ai/ha or less, 420 g ai/ha or less, 410 g ai/ha or less, 400 g ai/ha or less, 390 g ai/ha or less, 380 g ai/ha or less, 370 g ai/ha or less, 360 g ai/ha or less, 350 g ai/ha or less, 340 g ai/ha or less, 330 g ai/ha or less, 320 g ai/ha or less, 310 g ai/ha or less, 300 g ai/ha or less, 290 g ai/ha or less, 280 g ai/ha or less, 270 g ai/ha or less, 260 g ai/ha or less, 250 g ai/ha or less, 240 g ai/ha or less, 230 g ai/ha or less, 220 g ai/ha or less, 210 g ai/ha or less, 200 g ai/ha or less, 195 g ai/ha or less, 190 g ai/ha or less, 185 g ai/ha or less, 180 g ai/ha or less, 175 g ai/ha or less, 170 g ai/ha or less, 165 g ai/ha or less, 160 g ai/ha or less, 155 g ai/ha or less, 150 g ai/ha or less, 145 g ai/ha or less, 140 g ai/ha or less, 135 g ai/ha or less, 130 g ai/ha or less, 125 g ai/ha or less, 120 g ai/ha or less, 115 g ai/ha or less, 110 g ai/ha or less, 105 g ai/ha or less, 100 g ai/ha or less, 95 g ai/ha or less, 90 g ai/ha or less, 85 g ai/ha or less, 80 g ai/ha or less, 75 g ai/ha or less, 70 g ai/ha or less, 65 g ai/ha or less, 60 g ai/ha or less, 55 g ai/ha or less, 50 g ai/ha or less, 45 g ai/ha or less, 40 g ai/ha or less, 35 g ai/ha or less, or 30 g ai/ha or less).

The second pesticide (b) or an agriculturally acceptable salt or ester thereof can be applied to vegetation or an area adjacent the vegetation or applied to soil to prevent the emergence or growth of vegetation in an amount ranging from any of the minimum values described above to any of the maximum values described above. In some embodiments, (b) or agriculturally acceptable salt or ester thereof is applied to vegetation or an area adjacent the vegetation or applied to soil to prevent the emergence or growth of vegetation in an amount of from 25-500 g ai/ha (e.g., from 45-190 g ai/ha, from 50-180 g ai/ha, from 55-175 g ai/ha, from 60-170 g ai/ha, from 70-160 g ai/ha, from 75-150 g ai/ha, or from 84-150 g ai/ha).

In some embodiments, (a) penoxsulam or an agriculturally acceptable salt thereof is the sole pesticide applied to control undesirable vegetation in pineapple. In other embodiments, methods of controlling undesirable vegetation in pineapple comprise applying to vegetation or an area adjacent the vegetation or applying to soil to prevent the emergence or growth of vegetation (a) penoxsulam or an agriculturally acceptable salt thereof and (b) a second pesticide (e.g., an ACCase inhibitor) or an agriculturally acceptable salt or ester thereof. In certain embodiments, (b) includes cyhalofop, haloxyfop, fluazifop, or combinations thereof.

In some embodiments, the weight ratio of (a) penoxsulam or agriculturally acceptable salt thereof to (b) a second pesticide (e.g., cyhalofop, haloxyfop, fluazifop, or combinations thereof) or an agriculturally acceptable salt or ester thereof that is applied to control undesirable vegetation in pineapple is at least 1:100 (e.g., at least 1:95, at least 1:90, at least 1:85, at least 1:80, at least 1:75, at least 1:70, at least 1:65, at least 1:60, at least 1:55, at least 1:50, at least 1:45, at least 1:40, at least 1:35, at least 1:30, at least 1:25, at least 1:20, at least 1:15, at least 1:10, at least 1:9, at least 1:8, at least 1:7, at least 1:6, at least 1:5, at least 1:4, at least 1:3, at least 1:2, at least 1:1, or at least 1.5:1). In some embodiments, the weight ratio of (a) to (b) that is applied to control undesirable vegetation in pineapple is 2:1 or less (e.g., 1.5:1 or less, 1:1 or less, 1:2 or less, 1:3 or less, 1:4 or less, 1:5 or less, 1:6 or less, 1:7 or less, 1:8 or less, 1:9 or less, 1:10 or less, 1:15 or less, 1:20 or less, 1:25 or less, 1:30 or less, 1:35 or less, 1:40 or less, 1:45 or less, 1:50 or less, 1:55 or less, 1:60 or less, 1:65 or less, 1:70 or less, 1:75 or less, 1:80 or less, 1:85 or less, 1:90 or less, or 1:95 or less).

The weight ratio of (a) penoxsulam or agriculturally acceptable salt thereof to (b) a second pesticide or an agriculturally acceptable salt or ester thereof that is applied to control undesirable vegetation in pineapple can range from any of the minimum ratios described above to any of the maximum values described above. In some embodiments, the weight ratio of (a) penoxsulam or agriculturally acceptable salt thereof to (b) a second pesticide or an agriculturally acceptable salt or ester thereof that is applied to control undesirable vegetation in pineapple is from 1:100 to 2:1 (e.g., from 1:12 to 1:2, from 1:3 to 1:9, or from 1:4 to 1:8).

Formulations

The present disclosure also relates to formulations for use in conjunction with the methods disclosed herein.

In some embodiments, the formulation can be in the form of a single package formulation including (a) penoxsulam or an agriculturally acceptable salt thereof and optionally (b) a second pesticide or an agriculturally acceptable salt or ester thereof. In some embodiments, the formulation can be in the form of a single package formulation including both (a) and (b) and further including at least one additive. In some embodiments, the formulation can be in the form of a two-package formulation, wherein one package contains (a) and optionally at least one additive while the other package contains (b) and optionally at least one additive. In some embodiments of the two-package formulation, the formulation including (a) and optionally at least one additive and the formulation including (b) and optionally at least one additive are mixed before application and then applied simultaneously. In some embodiments, the mixing is performed as a tank-mix (i.e., the formulations are mixed immediately before or upon dilution with water). In some embodiments, the formulation including (a) and the formulation including (b) are not mixed but are applied sequentially (in succession), for example, immediately or within 1 hour, within 2 hours, within 4 hours, within 8 hours, within 16 hours, within 24 hours, within 2 days, or within 3 days of each other.

In some embodiments, the formulation of (a) and/or (b) is present in suspended, emulsified, or dissolved form. Exemplary formulations include, but are not limited to, aqueous solutions, powders, suspensions, also highly-concentrated aqueous, oily or other suspensions or dispersions, aqueous emulsions, aqueous microemulsions, aqueous suspo-emulsions, oil dispersions, pastes, dusts, and materials for spreading or granules.

In some embodiments, (a) penoxsulam or an agriculturally acceptable salt thereof and/or (b) a second pesticide or an agriculturally acceptable or ester salt thereof is an aqueous solution that can be diluted before use. In some embodiments, (a) and/or (b) is provided as a high-strength formulation such as a concentrate. In some embodiments, the concentrate is stable and retains potency during storage and shipping. In some embodiments, the concentrate is a clear, homogeneous liquid that is stable at temperatures of 54° C. or greater. In some embodiments, the concentrate does not exhibit any precipitation of solids at temperatures of −10° C. or higher. In some embodiments, the concentrate does not exhibit separation, precipitation, or crystallization of any components at low temperatures. For example, the concentrate remains a clear solution at temperatures below 0° C. (e.g., below −5° C., below −10° C., below −15° C.). In some embodiments, the concentrate exhibits a viscosity of less than 50 centipoise (50 megapascals), even at temperatures as low as 5° C.

In some embodiments, (a) penoxsulam or an agriculturally acceptable salt thereof is provided in a premixed formulation with cyhalofop (e.g., cyhalofop-butyl), haloxyfop (e.g., haloxyfop-methyl), or combinations thereof. Exemplary premixes of penoxsulam or an agriculturally acceptable salt thereof and cyhalofop that are or have been commercially available include, but are not limited to, CLINTON® (a premix incorporating cyhalofopbutyl by Dow AgroSciences LLC) and REBELEX® (a premix incorporating cyhalofopbutyl by Dow AgroSciences LLC).

In some embodiments, (a) penoxsulam or an agriculturally acceptable salt thereof and/or (b) a second pesticide or an agriculturally acceptable salt or ester thereof can also be mixed with or applied with an additive. In some embodiments, the additive can be diluted in water or can be concentrated. In some embodiments, the additive is added sequentially. In some embodiments, the additive is added simultaneously. In some embodiments, the additive is premixed with the penoxsulam or agriculturally acceptable salt thereof. In some embodiments, the additive is premixed with the second pesticide or agriculturally acceptable salt or ester thereof. In some embodiments, the additive is premixed with the penoxsulam or agriculturally acceptable salt thereof and the second pesticide or agriculturally acceptable salt or ester thereof.

In some embodiments, the additive is an additional pesticide. Exemplary additional pesticides include, but are not limited to, 2,4-D, acetochlor, aclonifen, amicarbazone, 4-aminopicolinic acid based herbicides, such as halauxifen, halauxifen-methyl, and those described in U.S. Pat. Nos. 7,314,849 and 7,432,227 to Balko et al., amidosulfuron, aminocyclopyrachlor, aminopyralid, aminotriazole, ammonium thiocyanate, asulam, atrazine, beflubutamid, benazolin, bensulfuron-methyl, bentazone, bifenox, bromacil, bromoxynil, butachlor, butafenacil, butralin, butroxydim, carbetamide, carfentrazone, carfentrazone-ethyl, chlormequat, clopyralid, chlorsulfuron, chlortoluron, cinidon-ethyl, clethodim, clodinafop-propargyl, clomazone, cyanazine, cyclosulfamuron, cycloxydim, dicamba, dichlobenil, dichlorprop-P, diclofop-methyl, diclosulam, diflufenican, diflufenzopyr, dimefuron, dimethachlor, diquat, diuron, S-ethyl dipropylcarbamothioate (EPTC), ethoxysulfuron, fenoxaprop, fenoxaprop-ethyl, fenoxaprop-ethyl+isoxadifen-ethyl, fenoxaprop-P-ethyl, fenoxasulfone, flazasulfuron, florasulam, flucarbazone, flucarbazone-sodium, flucetosulfuron (LGC-42153), flufenacet, flumetsulam, flumioxazin, flupyrsulfuron, flurochloridone, fluroxypyr, fluroxypyrmeptyl, flurtamone, glufosinate, glufosinate-ammonium, glyphosate, hexazinone, imazamethabenz, imazamox, imazapic, imazapyr, imazaquin, imazethapyr, imazosulfuron, indanofan, indaziflam, iodosulfuron, iodosulfuron-ethyl-sodium, ioxynil, isoproturon, isoxaben, isoxaflutole, lactofen, linuron, MCPA, MCPB, mecoprop-P, mesosulfuron, mesosulfuron-ethyl sodium, metazochlor, metosulam, metribuzin, metsulfuron, metsulfuron-methyl, MSMA, napropamide, napropamide-M, norfurazon, orthosulfamuron, oryzalin, oxadiargyl, oxadiazon, oxyfluorfen, paraquat, pendimethalin, picloram, picolinafen, pinoxaden, primisulfuron, profluazol, propaquizafop, propoxycarbazone, propyzamide, prosulfocarb, prosulfuron, pyraflufen-ethyl, pyrasulfotole, pyribenzoxim (LGC-40863), pyroxsulam, pyroxasulfone, quinmerac, quizalofop-ethyl-D, quizalofop-P-ethyl, quizalofop-P-tefuryl, rimsulfuron, sethoxydim, simazine, sulfentrazone, sulfometuron, sulfosate, sulfosulfuron, tebuthiuron, tepraloxydim, terbacil, terbuthylazine, terbutryn, thiazopyr, thifensulfuron, thifensulfuron-methyl, topramezone, tralkoxydim, triasulfuron, tribenuron, tribenuron-methyl, triafamone, triclopyr, and trifluralin, and agriculturally acceptable salts, esters and mixtures thereof.

In some embodiments, the additional pesticide further includes an additional acetolactate synthase (ALS) inhibitor that is applied in combination with the ACCase inhibitor. Exemplary ALS inhibitors include azimsulfuron, bispyribac-sodium, bensulfuron-methyl, cinosulfuron, cloransulam-methyl, diclosulam, ethoxysulfuron, flazasulfuron, florasulam, flumetsulam, halosulfuron-methyl, imazamox, imazethapyr, imazosulfuron, iofensulfuron, metazosulfuron, metsulfuron-methyl, orthosulfamuron, propyrisulfuron, pyrazosulfuron-ethyl, pyribenzoxim, pyriftalid, pyriminobac-methyl, pyrimisulfan, pyroxsulam and triafamone.

In some embodiments, the additional pesticide includes oxyfluorfen, triclopyr, bentazone, fenoxaprop, fomesafen, and agriculturally acceptable salts, esters and mixtures thereof. In certain embodiments, the additional pesticide is not an ACCase inhibitor.

In some embodiments, the penoxsulam or an agriculturally acceptable salt thereof is provided in a premixed formulation with an additional pesticide. In some embodiments, the penoxsulam or an agriculturally acceptable salt thereof is premixed with, oxyfluorfen, triclopyr, or combinations thereof. Exemplary premixes of penoxsulam or an agriculturally acceptable salt thereof and an additive that are or have been commercially available include, but are not limited to, TOPSHOT® (a premix incorporating cyhalofop-butyl by Dow AgroSciences LLC), REBEL EX™ (a premix incorporating cyhalofop-butyl by Dow AgroSciences LLC), PINDAR® (a premix incorporating oxyfluorfen by Dow AgroSciences LLC) and GRASP® XTRA (a premix incorporating triclopyr by Dow AgroSciences LLC).

In some embodiments, the second pesticide or an agriculturally acceptable salt or ester thereof is provided in a premixed formulation with an additional pesticide. In some embodiments, the second pesticide is haloxyfop or an agriculturally acceptable salt or ester thereof that is provided in a premixed formulation with an additional pesticide. Exemplary premixes of haloxyfop or an agriculturally acceptable salt or ester thereof and an additive that are or have been commercially available include, but are not limited to, VULKAN ULTRA® (a premix incorporating bentazone by BASF Corporation).

In some embodiments, the second pesticide is fluazifop or an agriculturally acceptable salt or ester thereof that is provided in a premixed formulation with an additional pesticide. Exemplary premixes of fluazifop or an agriculturally acceptable salt or ester thereof and an additive that are or have been commercially available include, but are not limited to, FUSION® (a premix incorporating fenoxaprop-P-ethyl by Syngenta), HORIZON 2000® (a premix incorporating fenoxaprop-P-ethyl by Bayer CropScience), FUSI-FLEX® (a premix incorporating fomesafen by Syngenta), ROBUST® (a premix incorporating fomesafen by Syngenta), and TYPHOON® (a premix incorporating fomesafen by Syngenta).

In some embodiments, the additive includes an agriculturally acceptable adjuvant. Exemplary agriculturally acceptable adjuvants include, but are not limited to, antifreeze agents, antifoam agents, compatibilizing agents, sequestering agents, neutralizing agents and buffers, corrosion inhibitors, colorants, odorants, penetration aids, wetting agents, spreading agents, dispersing agents, thickening agents, freeze point depressants, antimicrobial agents, crop oil, safeners, adhesives (for instance, for use in seed formulations), surfactants, protective colloids, emulsifiers, tackifiers, and mixtures thereof. Exemplary agriculturally acceptable adjuvants include, but are not limited to, crop oil concentrate (mineral oil (85%) +emulsifiers (15%)) or less, nonylphenol ethoxylate or less, benzylcocoalkyldimethyl quaternary ammonium salt or less, blend of petroleum hydrocarbon, alkyl esters, organic acid, and anionic surfactant or less, $C_9$-$C_{11}$ alkylpolyglycoside or less, phosphate alcohol ethoxylate or less, natural primary alcohol ($C_{12}$-$C_{16}$) ethoxylate or less, di-sec-butylphenol EO-PO block copolymer or less, polysiloxane-methyl cap or less, nonylphenol ethoxylate+urea ammonium nitrate or less, emulsified methylated seed oil or less, tridecyl alcohol (synthetic) ethoxylate (8 EO) or less, tallow amine ethoxylate (15 EO) or less, and PEG(400) dioleate-99.

In some embodiments, the additive is a safener that is an organic compound leading to better crop plant compatibility when applied with a herbicide. In some embodiments, the safener itself is herbicidally active. In some, the safener acts as an antidote or antagonist in the crop plants and can reduce or prevent damage to the crop plants. Exemplary safeners include, but are not limited to, AD-67 (MON 4660), benoxacor, benthiocarb, brassinolide, cloquintocet (mexyl), cyometrinil, cyprosulfamide, daimuron, dichlormid, dicyclonon, dietholate, dimepiperate, disulfoton, fenchlorazole, fenchlorazole-ethyl, fenclorim, flurazole, fluxofenim, furilazole, harpin proteins, isoxadifen-ethyl, jiecaowan, jiecaoxi, mefenpyr, mefenpyr-diethyl, mephenate, naphthalic anhydride, 2,2,5-trimethyl-3-(dichloroacetyl)-1,3-oxazolidine, 4-(dichloroacetyl)-1-oxa-4-azaspiro[4.5]decane, oxabetrinil, 829148, and N-phenyl-sulfonylbenzoic acid amides, as well as agriculturally acceptable salts and, provided they have a carboxyl group, their agriculturally acceptable derivatives thereof. In some embodiments, the safener can be cloquintocet or an ester or salt thereof, such as cloquintocet (mexyl).

Exemplary surfactants (e.g., wetting agents, tackifiers, dispersants, emulsifiers) include, but are not limited to, the alkali metal salts, alkaline earth metal salts and ammonium salts of aromatic sulfonic acids, for example lignosulfonic acids, phenolsulfonic acids, naphthalenesulfonic acids, and dibutylnaphthalenesulfonic acid, and of fatty acids, alkyl- and alkylarylsulfonates, alkyl sulfates, lauryl ether sulfates and fatty alcohol sulfates, and salts of sulfated hexa-, hepta- and octadecanols, and also of fatty alcohol glycol ethers, condensates of sulfonated naphthalene and its derivatives with formaldehyde, condensates of naphthalene or of the naphthalene sulfonic acids with phenol and formaldehyde, polyoxyethylene octylphenol ether, ethoxylated isooctyl-, octyl- or nonylphenol, alkylphenyl or tributylphenyl polyglycol ether, alkyl aryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignosulfite waste liquors and proteins, denatured proteins, polysaccharides (e.g., methylcellulose), hydrophobically modified starches, polyvinyl alcohol, polycarboxylates, polyalkoxylates, polyvinyl amine, polyethyleneimine, polyvinylpyrrolidone and copolymers thereof.

Exemplary thickeners include, but are not limited to, polysaccharides, such as xanthan gum, and organic and inorganic sheet minerals, and mixtures thereof.

Exemplary antifoam agents include, but are not limited to, silicone emulsions, long-chain alcohols, fatty acids, salts of fatty acids, organofluorine compounds, and mixtures thereof.

Exemplary antimicrobial agents include, but are not limited to, bactericides based on dichlorophen and benzyl alcohol hemiformal, and isothiazolinone derivates, such as alkylisothiazolinones and benzisothiazolinones, and mixtures thereof.

Exemplary antifreeze agents, include, but are not limited to ethylene glycol, propylene glycol, urea, glycerol, and mixtures thereof.

Exemplary colorants include, but are not limited to, the dyes known under the names Rhodamine B, pigment blue 15:4, pigment blue 15:3, pigment blue 15:2, pigment blue 15:1, pigment blue 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108, and mixtures thereof.

Exemplary adhesives include, but are not limited to, polyvinylpyrrolidone, polyvinyl acetate, polyvinyl alcohol, tylose, and mixtures thereof.

In some embodiments, the additive includes a carrier. In some embodiments, the additive includes a liquid or solid carrier. In some embodiments, the additive includes an organic or inorganic carrier. Exemplary liquid carriers include, but are not limited to, petroleum fractions or hydrocarbons such as mineral oil, aromatic solvents, paraffinic oils, and the like or less, vegetable oils such as soybean oil, rapeseed oil, olive oil, castor oil, sunflower seed oil, coconut oil, corn oil, cottonseed oil, linseed oil, palm oil, peanut oil, safflower oil, sesame oil, tung oil and the like or less, esters of the above vegetable oils or less, esters of monoalcohols or dihydric, trihydric, or other lower polyalcohols (4-6 hydroxy containing), such as 2-ethyl hexyl stearate, n-butyl oleate, isopropyl myristate, propylene glycol dioleate, di-octyl succinate, di-butyl adipate, di-octyl phthalate and the like or less, esters of mono, di and polycarboxylic acids and the like, toluene, xylene, petroleum naphtha, crop oil, acetone, methyl ethyl ketone, cyclohexanone, trichloroethylene, perchloroethylene, ethyl acetate, amyl acetate, butyl acetate, propylene glycol monomethyl ether and diethylene glycol monomethyl ether, methyl alcohol, ethyl alcohol, isopropyl alcohol, amyl alcohol, ethylene glycol, propylene glycol, glycerine, N-methyl- 2-pyrrolidinone, N,N-dimethyl alkylamides, dimethyl sulfoxide, liquid fertilizers and the like, and water as well as mixtures thereof. Exemplary solid carriers include, but are not limited to, silicas, silica gels, silicates, talc, kaolin, limestone, lime, chalk, bole, loess, clay, dolomite, diatomaceous earth, calcium sulfate, magnesium sulfate, magnesium oxide, ground synthetic materials, pyrophyllite clay, attapulgus clay, kieselguhr, calcium carbonate, bentonite clay, Fuller's earth, cottonseed hulls, wheat flour, soybean flour, pumice, wood flour, walnut shell flour, lignin, ammonium sulfate, ammonium phosphate, ammonium nitrate, ureas, cereal meal, tree bark meal, wood meal and nutshell meal, cellulose powders, and mixtures thereof.

In some embodiments, emulsions, pastes or oil dispersions, can be prepared by homogenizing (a) and/or (b) in water by means of wetting agent, tackifier, dispersant or emulsifier. In some embodiments, concentrates suitable for dilution with water are prepared, comprising (a), optionally (b), a wetting agent, a tackifier, and a dispersant or emulsifier.

In some embodiments, powders or materials for spreading and dusts can be prepared by mixing or concomitant grinding of (a) and/or (b) and optionally a safener with a solid carrier.

In some embodiments, granules (e.g., coated granules, impregnated granules and homogeneous granules) can be prepared by binding the (a) and (b) to solid carriers.

The concentrations of (a) and (b), when present in the formulation, can be varied. In some embodiments, the formulations comprise from 1% to 95% (e.g., from 5% to 95%, from 10% to 80%, from 20% to 70%, from 30% to 50%) by total weight of (a) and (b), when present. In some embodiments, (a) and (b), when present, independently, can be employed in a purity of from 90% to 100% (e.g., from 95% to 100%) according to nuclear magnetic resonance (NMR) spectrometry. In some embodiments, the concentrations of (a), (b), when present, and additional pesticides in the formulations can be varied. In some embodiments, the formulations comprise from 1% to 95% (e.g., from 5% to 95%, from 10% to 80%, from 20% to 70%, from 30% to 50%) by total weight of (a), (b), when present, and additional pesticides. In some embodiments, (a), (b), when present, and additional pesticides, independently, can be employed in a purity of from 90% to 100% (e.g., from 95% to 100%) according to NMR spectrometry.

Methods of Application

The formulations described above containing (a) and/or (b) can be applied using any known technique for applying herbicides. Exemplary application techniques include, but are not limited to, spraying, atomizing, dusting, spreading, or direct application. The method of application can vary depending on the intended purpose. In some embodiments, the method of application can be chosen to ensure the finest possible distribution of the compositions disclosed herein.

The formulations disclosed herein can be applied pre-emergence (before the emergence of undesirable vegetation) or post-emergence (i.e., during and/or after emergence of the undesirable vegetation). In some cases, the formulations are applied to the undesirable vegetation when the undesirable vegetation has reached the 1-6 leaf stage.

Formulations containing (a) and/or (b) can be applied after seeding or transplanting and before or after the emergence of the pineapple plants and/or weeds. In some embodiments, the formulations show good crop tolerance (e.g., little to no phytotoxicity) even when the pineapple is actively growing. Accordingly, the formulations can be applied during or after the emergence of the pineapple plants to control undesirable vegetation.

In some embodiments, the formulations disclosed herein containing (a) and/or (b) are applied to pineapple vegetation or an area adjacent the vegetation or applied to soil to prevent the emergence or growth of vegetation by spraying (e.g., foliar spraying). In some embodiments, the spraying techniques use, for example, water as carrier and spray liquor rates of from 10 liters per hectare (L/ha) to 2000 L/ha (e.g., from 50 L/ha to 1000 L/ha, or from 100 to 500 L/ha). In some embodiments, the formulations disclosed herein are applied by the low-volume or the ultra-low-volume method, wherein the application is in the form of microgranules. In some embodiments, wherein the formulations disclosed herein are less well tolerated by certain pineapple plants, the formulations can be applied with the aid of the spray apparatus in such a way that they come into little contact, if any, with the leaves of the sensitive pineapple plants while reaching the leaves of undesirable vegetation that grows underneath or the bare soil (e.g., post-directed or lay-by).

In some embodiments, herbicidal activity is exhibited by (a) and optionally (b) when they are applied directly to the plant or to the locus of the plant at any stage of growth or before planting, emergence, or during plant growth up to harvest. The effect observed can depend upon the type of undesirable vegetation to be controlled, the stage of growth of the undesirable vegetation, the application parameters of dilution and spray drop size, the particle size of solid components, the environmental conditions at the time of use, the specific compound employed, the specific adjuvants and carriers employed, the soil type, and the like, as well as the amount of chemical applied. In some embodiments, these and other factors can be adjusted to promote non-selective or selective herbicidal action.

The methods disclosed herein can be used to control undesired vegetation in pineapple without significant crop damage. The methods disclosed herein can be used in pineapple crops that are resistant to, for instance, herbicides, pathogens, and/or insects. In some embodiments, the methods disclosed herein can be used in pineapple plants that are resistant to one or more herbicides because of genetic engineering or breeding. In some embodiments, the methods disclosed herein can be used in pineapple plants that are resistant to one or more pathogens such as plant pathogenous fungi owing to genetic engineering or breeding. In some embodiments, the methods disclosed herein can be used in pineapple plants that are resistant to attack by insects owing to genetic engineering or breeding.

In some embodiments, the compositions disclosed herein can be used for controlling broadleaf weeds, grass weeds, sedge weeds, and combinations thereof. In some cases, the undesirable vegetation is selected from praxelis (*Praxelis clematidea*, PXJCL), oriental fountain grass (*Pennisetum orientale*, PESOR), mission grass (*Pennisetum polystachion*, PESPO), broadleaf buttonweed (*Borreria latifolia*, BOILF), morning glory (*Ipomoea triloba*, IPOGR), crabgrass (*Digitaria ciliaris*, DIGSS), Guinea grass (*Panicum maximum*, PANMA), Southern sandbar (*Cenchrus echinatus*, CCHEC), signalgrass (*Brachiaria reptans*, BRASS), crowfoot grass (*Dactyloctenium aegyptium*, DTTAE), sweet broomweed (*Scoparia dulcis*, SCFDU), slender amaranth (*Amaranthus viridis*, AMAVI), and combinations thereof.

By way of non-limiting illustration, examples of certain embodiments of the present disclosure are given below.

EXAMPLES

Evaluation of Penoxsulam and Penoxsulam+Cyhalofop in Pineapple

Field trials were conducted in pineapple (*Ananas comosus*, Linn; ANHCO) plantations located in the Uthai Thani province of Thailand. All treatments were applied using a randomized complete block trial design, with 4 replications per treatment.

Treatments consisted of RAINBOW® 25OD (penoxsulam 2.5% OD) applied at 12.5 to 25 g ai/ha and TOPSHOT® 60OD (penoxsulam+cyhalofop-butyl, 1+5% OD) applied at 120 g ai/ha. Treatments were sprayed directly onto the pineapple crop and weeds, when the weeds had reached the 4-6 leaf stage. The phytotoxicity of the treatments was evaluated at 7, 14, 21, 28, 42, and 56 days after treatment application. Weed control evaluations were conducted between 45 and 56 days after treatment application.

The treated plots and control plots were rated blind at various intervals after application. Ratings were based on a scale of 0-100% wherein 0% indicates no control of the undesired vegetation and 100% indicates complete control of the undesired vegetation.

The results of the trials are summarized in Tables 1-2. Unexpectedly, RAINBOW® 25OD applied at 25 g ai/ha and TOPSHOT® 60OD applied at 120 g ai/ha provided good control of undesirable vegetation when applied post-emergence to the crop and weeds without any significant phytotoxicity or injury to pineapple.

TABLE 1

Percent Crop Injury (0-100 Scale) to Pineapple (ANHCO) from postemergence applications by visual rating at varying intervals after treatment

| Treatment | g ai/ha | Evaluation Interval (Days After Treatment Application) | | | | | |
|---|---|---|---|---|---|---|---|
| | | 7 Days | 14 Days | 21 Days | 28 Days | 42 Days | 56 Days |
| Untreated (control) | — | 0 | 0 | 0 | 0 | 0 | 0 |
| RAINBOW ® 25OD | 25 | 0 | 0 | 0 | 0 | 0 | 0 |
| TOPSHOT ® 60OD | 120 | 0 | 0 | 0 | 0 | 0 | 0 |

Percent Crop Injury = 0-100 scale, 0 = no injury and 100 = complete kill.
g ai/ha = grams active ingredient per hectare

TABLE 2

Percent weed control (0-100 scale) from postemergence applications at 56 days following treatment.

| Treatment | g ai/ha | % Weed Control at 56 Days after Treatment | | | | |
|---|---|---|---|---|---|---|
| | | DIGSS | PXJCL | PESOR | BOILF | IPOGR |
| Untreated | — | 0 | 0 | 0 | 0 | 0 |
| RAINBOW ® 25OD | 25 | 47 | 100 | 100 | 100 | 75 |
| TOPSHOT ® 60OD | 120 | 83 | 100 | 100 | 100 | 75 |

Percent Weed Control = 0-100 acale, where 0 = no control and 100 = complete control.
DIGSS = crabgrass, *Digitaria* sp.
PXJCL = praxelis, *Praxelis clematidea*
PESOR = oriental fountain grass, *Pennisetum prientale*
BOILF = broadleaf buttonweed, *Borreria latifolia*
IPOGR = morningglory, *Ipomoea triloba*
g ai/ha = grams active ingredient per hectare

Evaluation of Penoxsulam, Penoxsulam+Haloxyfop, and Penoxsulam+Fluazifop in Pineapple Field trials were conducted in pineapple (Ananas comosus, Linn; ANHCO) plantations located in the Prachuap Kiri Khan province of Thailand. All treatments were applied using a randomized complete block trial design, with 4 replications per treatment.

Treatments consisted of RAINBOW® 25OD (penoxsulam 2.5% OD) tank-mixed with GALLANT SUPER® 10.8EC (haloxyfop-P-methyl 10.8% EC) at 12.5+84.4 g ai/ha and RAINBOW®25OD tank-mixed with FUSILADE® 125EC (fluazifop-P-butyl) 18.75+150 g ai/ha, respectively. The treatments were sprayed directly onto the pineapple crop and weeds when the weeds had reached the 4-6 leaf stage. The phytotoxicity of the treatments was evaluated at 15, 30, 45, and 60 days after treatment application. Weed control evaluations were performed at 45 days after treatment application.

The treated plots and control plots were rated blind at various intervals after application. Ratings were based on a scale of 0-100%, as discussed above, wherein 0% indicates no control of the undesired vegetation and 100% indicates complete control of the undesired vegetation.

The results of the trials are summarized in Tables 3-4. Unexpectedly, tank mixtures of penoxsulam (RAINBOW® 25OD) plus haloxyfop (GALLANT SUPER® 10.8EC) and penoxsulam (RAINBOW® 25OD) plus fluazifop-P-butyl (FUSILADE® 125EC) provided good control of undesirable vegetation when applied post-emergence to the pineapple crop and weeds without significant phytotoxicity to pineapple.

TABLE 3

Percent Crop Injury to Pineapple (ANHCO) from postemergence applications by visual rating at varying intervals after treatment

| Treatment | g ai/ha | Evaluation Interval (Days After Treatment Application) | | | |
|---|---|---|---|---|---|
| | | 15 Days | 30 Days | 45 Days | 60 Days |
| Untreated (control) | — | 0 | 0 | 0 | 0 |
| Hand Weeding | — | 0 | 0 | 0 | 0 |
| RAINBOW ® 25 OD + GALLANT SUPER ® 10.8 EC | 12.5 + 84.4 | 0 | 0 | 0 | 0 |
| RAINBOW ® 25 OD + FUSILADE ® 125 EC | 18.75 + 150 | 0 | 0 | 0 | 0 |

Percent Crop Injury = 0-100 scale 0 = no injury and 100 = complete kill.
g ai/ha = grams active ingredient per hectare

TABLE 4

Percent weed control (0-100 scale) from postemergence applications at 45 days following treatment.

| Treatment | g ai/ha | % Weed Control at 45 Days after Treatment | | | | | | |
|---|---|---|---|---|---|---|---|---|
| | | PANMA | CCHEC | BRASS | DTTAE | PXJCL | SCFDU | AMAVI |
| Untreated (control) | — | 0 | 0 | 0 | 0 | 0 | 0 | 0 |
| Hand Weeding | — | 100 | 100 | 100 | 100 | 45 | 100 | 100 |
| RAINBOW ® 25OD + GALLANT SUPER ® 10.8 EC | 12.5 + 84.4 | 100 | 100 | 100 | 100 | 59 | 30 | 100 |
| RAINBOW ® 25OD + FUSILADE ® 125EC | 18.75 + 150 | 100 | 100 | 100 | 100 | 100 | 100 | 100 |

Percent Weed Control = 0-100 scale, where 0 = no control and 100 = complete control.
PANMA = Guinea grass, *Panicum maximum*
CCHEC = Southern sandbur, *Cenchrus echinatus*
BRASS = signalgrass, *Brachiaria reptans*.
DTTAE = crowfootgrass, *Dactyloctenium aegyptium*
PXJCL = praxelis, *Praxelis clematidea*
SCFDU = sweet broomweed, *Scoparia dulcis*
AMAVI = slender amaranth, *Amaranthus viridis*
g ai/ha = grams active ingredient per hectare The compositions and methods of the appended claims are not limited in scope by the specific compositions and methods described herein, which are intended as illustrations of a few aspects of the claims and any compositions and methods that are functionally equivalent are intended to fall within the scope of the claims. Various modifications of the compositions and methods in addition to those shown and described herein are intended to fall within the scope of the appended claims. Further, while only certain representative compositions and method steps disclosed herein are specifically described, other combinations of the compositions and method steps also are intended to fall within the scope of the appended claims, even if not specifically recited. Thus, a combination of steps, elements, components, or constituents may be explicitly mentioned herein or less, however, other combinations of steps, elements, components, and constituents are included, even though not explicitly stated. The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments of the invention and are also disclosed. Other than in the examples, or where otherwise noted, all numbers expressing quantities of ingredients, reaction conditions, and so forth used in the specification and claims are to be understood at the very least, and not as an attempt to limit the application of the doctrine of equivalents to the scope of the claims, to be construed in light of the number of significant digits and ordinary rounding approaches.

What is claimed is:

1. A method of controlling undesirable vegetation in a pineapple crop comprising directly applying to the pineapple crop and to either the undesirable vegetation, an area adjacent the undesirable vegetation, or to the soil adjacent to the undesirable vegetation, a herbicidally effective amount of (a) penoxsulam, or an agriculturally acceptable salt thereof, wherein (a) is applied in an amount of 5 g ai/ha or greater.

2. The method of claim 1, wherein (b) a second pesticide or an agriculturally acceptable salt or ester thereof is applied to the vegetation or the area adjacent the vegetation, or to the soil adjacent thereto.

3. The method of claim 2, wherein (a) and (b) are applied simultaneously.

4. The method of claim 2, wherein (b) includes an ACCase inhibitor.

5. The method of claim 2, wherein (b) includes cyhalofop, haloxyfop, fluazifop, agriculturally acceptable esters or salts thereof, or combinations thereof.

6. The method of claim 2, wherein (b) includes cyhalofop-butyl.

7. The method of claim 2, wherein (b) includes haloxyfop-P-methyl.

8. The method of claim 2, wherein (b) includes fluazifop-P-butyl.

9. The method of claim 2, wherein (a) and (b) are applied in a weight ratio of (a) to (b) from 1:100 to 2:1.

10. The method of claim 2, wherein (a) and (b) are applied in a weight ratio of (a) to (b) from 1:12 to 1:4.

11. The method of claim 2, wherein (b) is applied in an amount of from 25-500 g ai/ha.

12. The method of claim 2, wherein (b) is applied in an amount of from 84-150 g ai/ha.

13. The method of claim 2, wherein (a) and (b), are applied post-emergence to the undesirable vegetation.

14. The method of claim 1, wherein the undesirable vegetation includes a broadleaf weed.

15. The method of claim 1, wherein the undesirable vegetation includes a grass weed.

16. The method of claim 1, wherein the undesirable vegetation includes a sedge weed.

17. The method of claim 1, wherein the undesirable vegetation includes praxelis, oriental fountain grass, mission grass, broadleaf buttonweed, morning glory, crabgrass, Guinea grass, crowfoot grass, slender amaranth, Southern sandbur, signalgrass, sweet broomweed, and combinations thereof.

18. The method of claim 1, wherein (a) is applied in an amount of from 5-50 g ai/ha.

19. The method of claim 1, wherein (a) is applied in an amount of from 12.5-25 g ai/ha.

20. The method of claim 1, further comprising applying a herbicide safener, an agriculturally acceptable adjuvant or carrier, or a combination thereof.

* * * * *